United States Patent [19]

Klaue

[11] Patent Number: 4,493,317
[45] Date of Patent: Jan. 15, 1985

[54] SURGICAL COMPRESSION PLATE AND DRILL GUIDE

[75] Inventor: Kaj Klaue, Sierre, Switzerland

[73] Assignee: Synthes Ltd. (U.S.A.), Wayne, Pa.

[21] Appl. No.: 321,602

[22] Filed: Nov. 16, 1981

[30] Foreign Application Priority Data

Nov. 20, 1980 [CH] Switzerland .......................... 8599/80

[51] Int. Cl.³ .......................... A61F 5/04; A61B 17/18
[52] U.S. Cl. .............................. 128/92 D; 128/92 B; 128/92 EB
[58] Field of Search ................. 128/92 D, 92 R, 92 B, 128/92 BA, 92 BB, 92 E, 92 EB

[56] References Cited

U.S. PATENT DOCUMENTS

| Re. 28,841 | 6/1976 | Allgower et al. ................ 128/92 D |
| 3,779,240 | 12/1973 | Kondo .............................. 128/92 D |
| 4,119,092 | 10/1978 | Gil ..................................... 128/92 D |

FOREIGN PATENT DOCUMENTS

| 16338 | 10/1980 | European Pat. Off. . |
| 2340880 | 8/1973 | Fed. Rep. of Germany ... 128/92 D |
| 1505513 | 11/1967 | France .............................. 128/92 D |
| 2233973 | 1/1975 | France .............................. 128/92 D |
| 2480106 | 4/1981 | France . |
| 373516 | 1/1964 | Switzerland . |
| 462375 | 10/1968 | Switzerland . |
| 468824 | 4/1969 | Switzerland . |
| 566767 | 9/1975 | Switzerland ...................... 128/92 D |
| 600862 | 6/1978 | Switzerland . |
| 611147 | 5/1979 | Switzerland . |
| 613616 | 10/1979 | Switzerland . |
| 613858 | 10/1979 | Switzerland . |
| 1153090 | 5/1969 | United Kingdom . |
| 1601383 | 10/1979 | United Kingdom . |

OTHER PUBLICATIONS

"The Use of My Compression Plate for Osteosyntheses of the Various Types of Femoral Intertrochateric Osteotomies" by A. Bertolin, La Clinica Ortopedica, vol. XVIII, Fasc 3, May–Jun. 1966, pp. 221–231.
Descamps, La Normalisation de vis, Plaques, Rondelles et Ecrous Utilises en Osteosynthese, J. Chir, (Paris), Jul.–Aug. 1970, t. 100, No. 1-2, pp. 43–60.
*Manual of Internal Fixation,* Mueller et al., 2nd Edition (eighth version), Springer–Verlay, Berlin, Heidelbert, New York, 1979, pp. 70–79.
Claudi et al., Helv. Chir. Acta 46, 177–182 (1979).
Bertolin, *La Clinica Ortopedica,* Vol. XVII, Fasc 3, May–June 1966, pp. 221–231.
Bagby, Staff Meetings of the Mayo Clinic 32, No. 3, Feb. 6, 1957, pp. 55–57.
Bagby et al., American Journal of Surgery 95, No. 5, 761–777 (1958), Reprint.

*Primary Examiner*—Ronald L. Frinks
*Attorney, Agent, or Firm*—Davis Hoxie Faithfull & Hapgood

[57] ABSTRACT

A surgical compression plate is provided which is designed to permit the insertion of bone screws at angles up to 45°. A drill guide capable of tilting to various angles, for use in connection with the novel plate is also disclosed.

11 Claims, 11 Drawing Figures

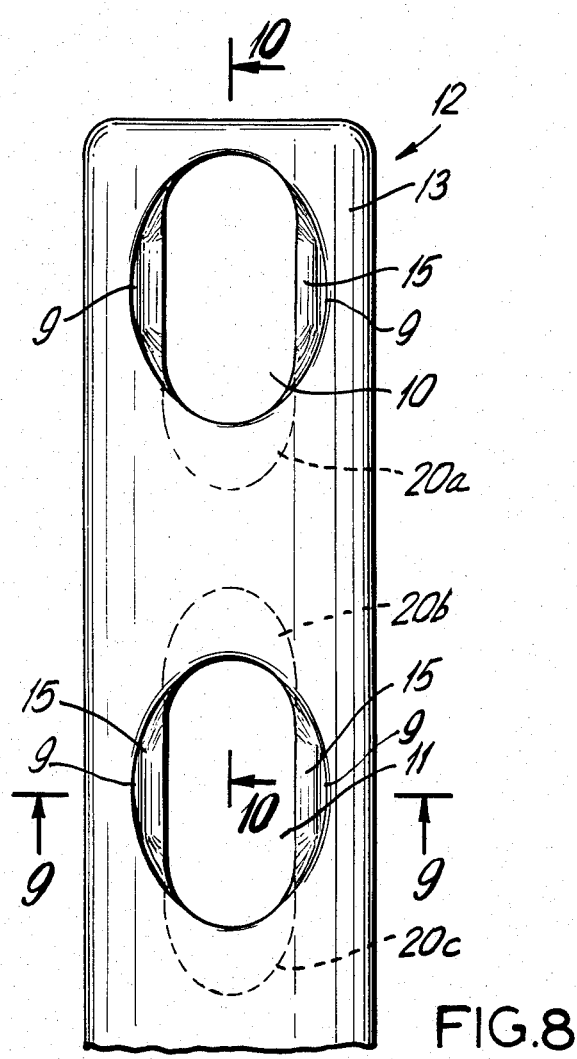
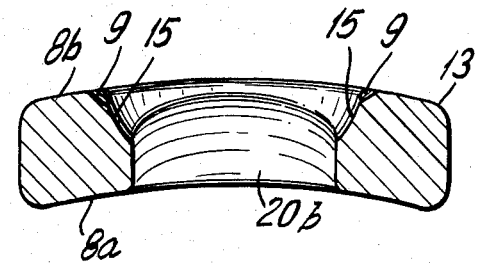
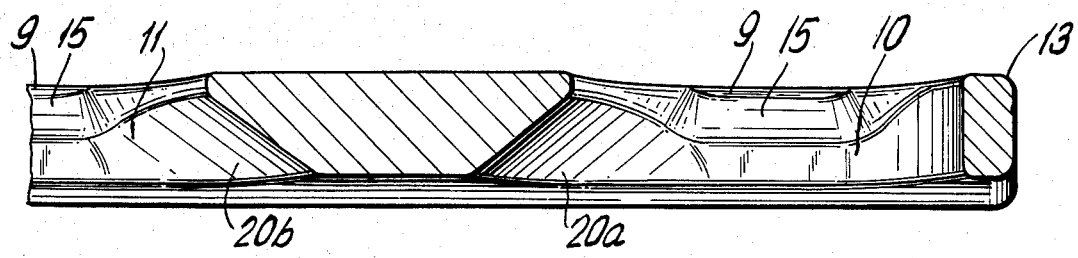
FIG. 8
FIG. 9
FIG. 10

SURGICAL COMPRESSION PLATE AND DRILL GUIDE

The invention relates to a device for the stabilization of a broken bone or for compression osteosynthesis in connection with osteotomies and to a drill guide for drilling holes in bones to be stabilized by means of said device.

At the present time in compression osteosynthesis compression plates are predominantly used in accordance with the principle of the tension band. In this technique the plate is conventionally mounted opposite the area to be stabilized on the side of the bone to be tensioned, after pre-tensioning, by means of screws perpendicular to the longitudinal axes of the bone and plate. The muscles opposite the plate as well as the physiological stress closes the fracture through additional dynamic compression. (See Manual of Internal Fixation, Müller et al., Springer-Verlag N.Y., 1979, p. 58, 59).

Static interfragmentary compression can be achieved through simple tension screws without using a plate. (See Claudi et al., Hel. Chir. Acta, 46, (1979), p. 177-182).

Recently it has also been proposed that stabilization by means of a plate could be improved through addition of an inclined tension screw, running obliquely to the longitudinal axes of the bone and plate, that penetrated through the fracture plane; the axial force of said screw produces additional interfragmentary compression. (See Claudi et al., supra, p. 178 and FIG. 2B).

This last method is limited in its applications since the geometry of conventional compression plates and screws have not permitted sufficient tilting of the screws in the holes of the compression plates with reference to a plane transverse to the axis of the plate, and have permitted practically no longitudinal movement of the screw in a tilted and fully screwed-in position, particularly when the screw was threaded along its entire length.

It has been found that it is necessary for a generally effective application of inclined tension screws, whether as the exclusive or as supplemental compression elements, that the screws be tiltable in the holes of the plates by up to 45° to the longitudinal axis of the hole, and that they be movable in the longitudinal direction of the hole in the fully screwed-in position over a significant distance.

It is an object of the present invention to provide a surgical plate for the stabilization of bones and for compression osteosynthesis in connection with osteotomies which will accommodate screws inserted at an angle of up to 45° and which will permit movement of screws angularly inserted, in the direction of the plate axis.

It is another object of the invention to provide a system for stabilizing bones and for compression osteosynthesis in connection with osteotomies comprising a plate and screws having a geometric relationship such that the screws may be inserted through the plates at angles up to 45° and be capable of translation axially of the plates.

It is another object of the invention to provide a device for guiding bone drills suitable for making inclined holes in bones to be stabilized with the plates as described.

In accordance with the invention these and other objects are achieved by means of a device comprising an elongated plate having a bottom surface for application to a bone, a plurality of elongated holes in said plate, each of said holes having surfaces along each side sloping downwardly and inwardly to provide for sliding movement, axially of said plate, of the heads of screws inserted in said holes, and a bevelled surface on the bottom of each of said holes at at least one end thereof.

The invention further comprises a system for the stabilization of broken bones and for compression osteosynthesis in connection with osteotomies comprising a plate as described and a plurality of screws having heads adapted to engage the sloping surfaces on the sides of the holes.

The invention further comprises a drill guide for drilling holes in a bone for the application of a plate, said plate having elongated holes with downwardly and inwardly sloping side walls, said guide comprising a drill socket and a ball-shaped bearing, said socket being attached to the bearing in a position eccentric to the center of the ball, and said ball being adapted to fit into the holes in the plate with the walls of the hole bearing on the sloping surfaces on the sides of the holes in the plate.

In a system according to the invention, the dimensions of the screw and plate hole are such that the screw is capable of translation axially of the plate by a distance at least ⅓ the diameter of the screw. Thus the longitudinal length of the plate hole must be greater than the width of the hole by at least one-third the width. Preferably the screws intended as tensioning screws have a smooth, unthreaded section immediately below the screw head which is at least as great in diameter as the diameter of the largest threaded section. It is contemplated that other screws may be provided for fixing the plate to the bone. Such screws, inserted normally to the plate, may have threads from the head to the tip along their entire length.

Preferably, the sloping walls of the plate holes have a cylindrical configuration, i.e., they are defined at least in part by a concave cylindrical surface, the axis of the cylinder being parallel to the axis of the plate or coinciding with the plate axis.

Alternatively the sloping surfaces may be compound surfaces formed by two planes which intersect along a straight line parallel to the axis of the plate.

Preferably, the edges of the holes on the upper side of the plate, i.e., the side away from the bone, are bevelled towards the outside, that is, the holes are flared towards the outside in such manner that the flared surface is shaped like a funnel. Preferably, the edges of the holes on the bottom of the plate, i.e., the side next to the bone are also bevelled, particularly on the side of the hole near the fracture. In this case the flare preferably also forms a part of a funnel.

In the drill guide according to the invention the radius of the ball-shaped bearing is preferably equal to the radius of the hemispherical head of the screw to be used. Thus, the ball-shaped bearing can lie in the holes of the plate at the end of the hole near the fracture during drilling, contacting the sloping, and preferably cylindrical, surface.

The invention will be further described in connection with the accompanying drawings which show the invention applied to bones of tubular structure and in which:

FIG. 8 is a plan view of a fragment of a plate according to the invention;

FIG. 9 is a view in transverse vertical section of a plate according to the invention, showing details of a hole;

FIG. 10 is a view in longitudinal vertical section of the plate fragment of FIG. 8;

Figure 11:
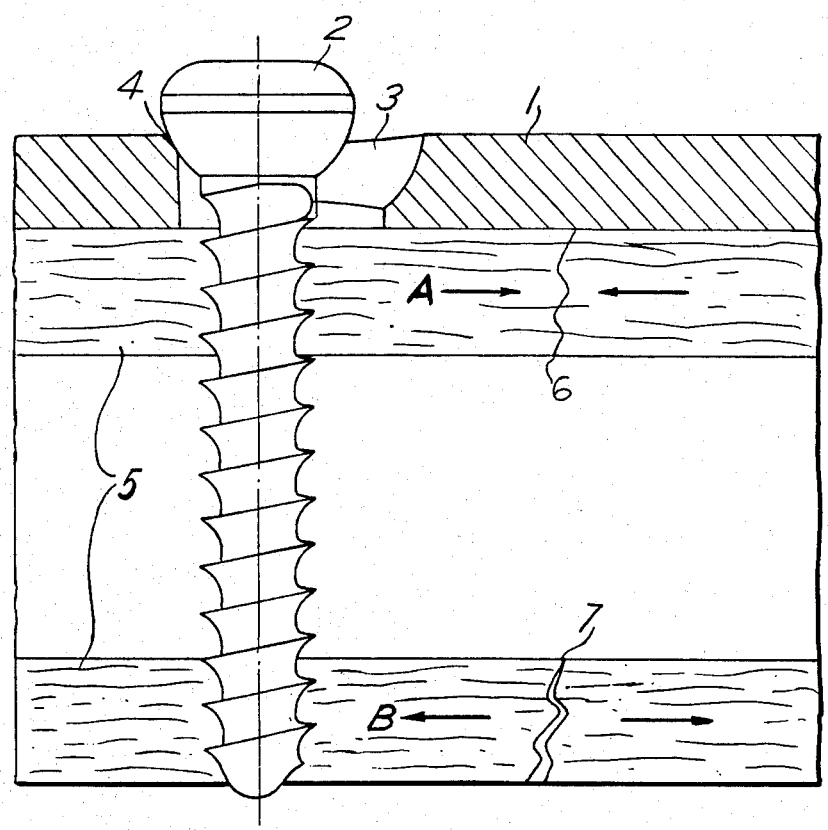
FIG. 11 is a view in longitudinal vertical section of a compression plate according to the prior art applied to a bone.

Referring first to FIG. 11, a length-wise section through a fracture treated by means of a dynamic compression plate such as that disclosed in U.S. Pat. No. Re. 28,841, is shown. Compression plate 1 which fits closely but not necessarily tightly to bone 5, has at least two holes (though only one hole, 3, is shown), and is fixed by means of a hemispherical headed screw 2 to the bone. The screw head abuts the edge 4 of the hole which edge forms part of a camming surface to shift the screw in the direction of the longitudinal axis of the plate. Tightening screw 2 to fix compression plate 1 causes the creation of opposing forces A and B at fracture points 6, 7. Force B, which pulls fracture point 7 away is undesirable. Attempts have been made to counter or eliminate forces such as B through various measures, such as bending the compression plate 1. See Claudi, supra.

Referring now to FIGS. 8–10 a plate 12, according to the invention, comprises a body portion 13. As may be seen best in FIG. 9, the plate is slightly curved in transverse cross section so that the lower surface 8a may be fitted to a bone, with the upper surface 8b away from the bone. The plate 12 has a plurality of elongated holes such as 10, 11. Each of the holes has a surface 15 on each side, which surface slopes downwardly and inwardly of the hole. Preferably, as shown in FIGS. 8–10, these surfaces conform to sections of a cylinder, so that, as explained in more detail below, they provide a congruent surface upon which the hemispherical head of a screw may slide.

The outer upper edges of the holes 10, 11 are preferably bevelled at 9. If the surfaces 15 are planar, then the bevelled sections 9 and the adjacent surfaces 15 form two intersecting planes whose line of intersection runs generally parallel to the axis of the plate 12.

On the underside 8a of the plate 12, the holes 10, 11 are bevelled, undercut or flared to give downwardly and outwardly sloping funnel-like surfaces such as 20a, 20b and 20c thus to accomodate a screw inserted at an angle of up to 45°. The end hole 10 has this undercut surface 20a at one end only since it is not generally expected that a screw would be inserted sloping toward the end of the plate. The internal hole 11, however, has undercut surfaces 20b and 20c at each end and is therefore symmetrical on both sides of a center line such as 9—9 across the width of the hole. It will be understood, of course, that holes which are not at the ends of the plate may be undercut at only one end, if desired. This variation is not shown.

While FIGS. 8–10 show the axis of the holes coincident with the axis of the plate, it is possible to have one or more of the hole axes oblique to the plate axis or at a right angle thereto.

Figure 1:
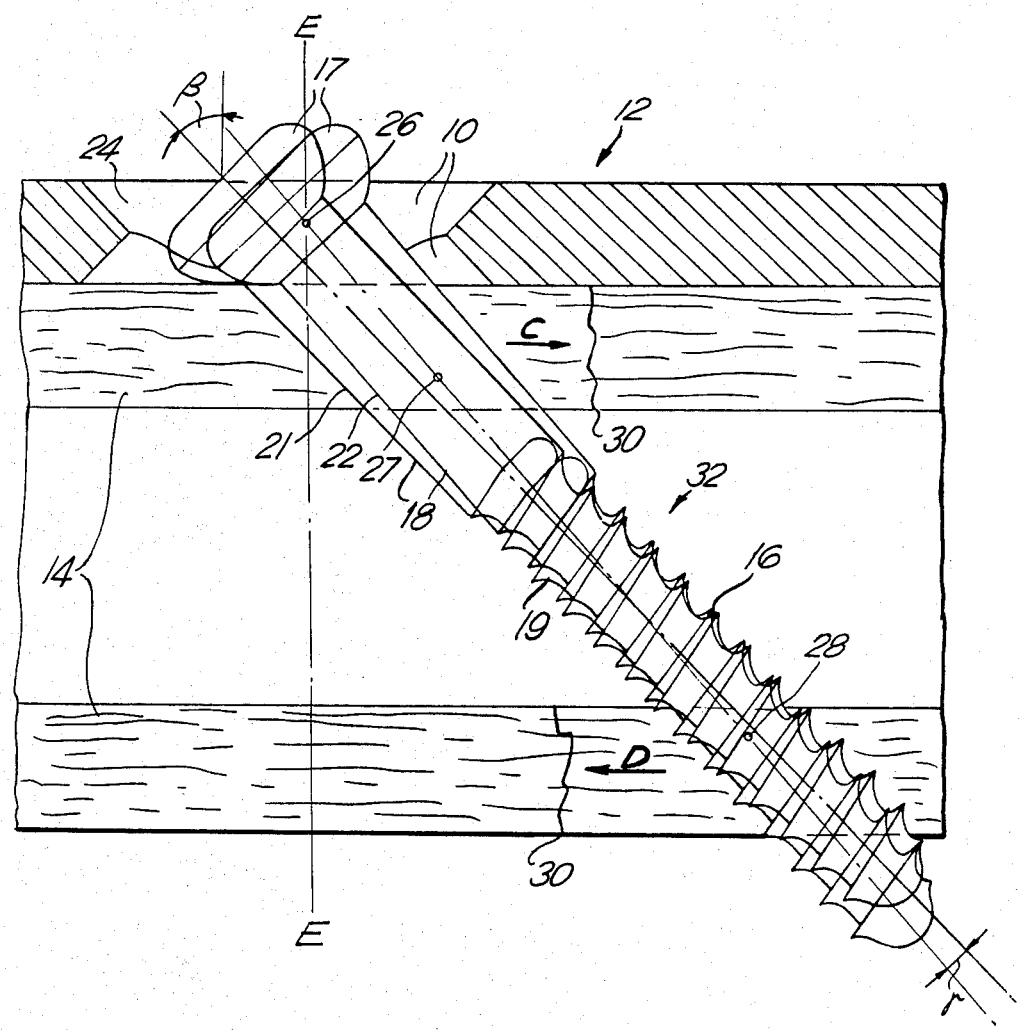
FIG. 1 is a schematic view in vertical longitudinal section of a part of a bone to which a system according to the invention has been applied, showing the forces and movements arising from application of a transverse compression screw according to the invention.

Referring now to FIG. 1, this Figure illustrates the opposing forces which arise upon application of an angularly directed screw in a plate according to the invention, these forces being indicated by the arrows C and D. In FIG. 1 a plate 12, according to the invention, has a plurality of elongated holes of which only one, 10, is shown. The plate is positioned snugly but not necessarily tightly on bone 14. A screw 16, having a smooth, unthreaded portion 18 between its head 17 and the thread 19, is set transversly into bone 14 in such a manner that it forms an angle of inclination $\beta$ of 45° with a plane E perpendicular to the longitudinal axis of the hole. Screw 16 is shown in two positions, 21 and 22. Position 22 is achieved by translation of the screw, with the head 17 sliding on the sloping surface 24 of the hole. A lever effect arises from the sliding of screw 16, through which effect the screw axis is rotated by angle $\gamma$. The lever effect is as if the forces were to grip at points 26, 28 and as if 27 were the fulcrum of the lever. The resulting forces C, D, in contrast to forces A, B of FIG. 4, press the fracture fragments together at all points to close the fracture 30.

Figure 2:
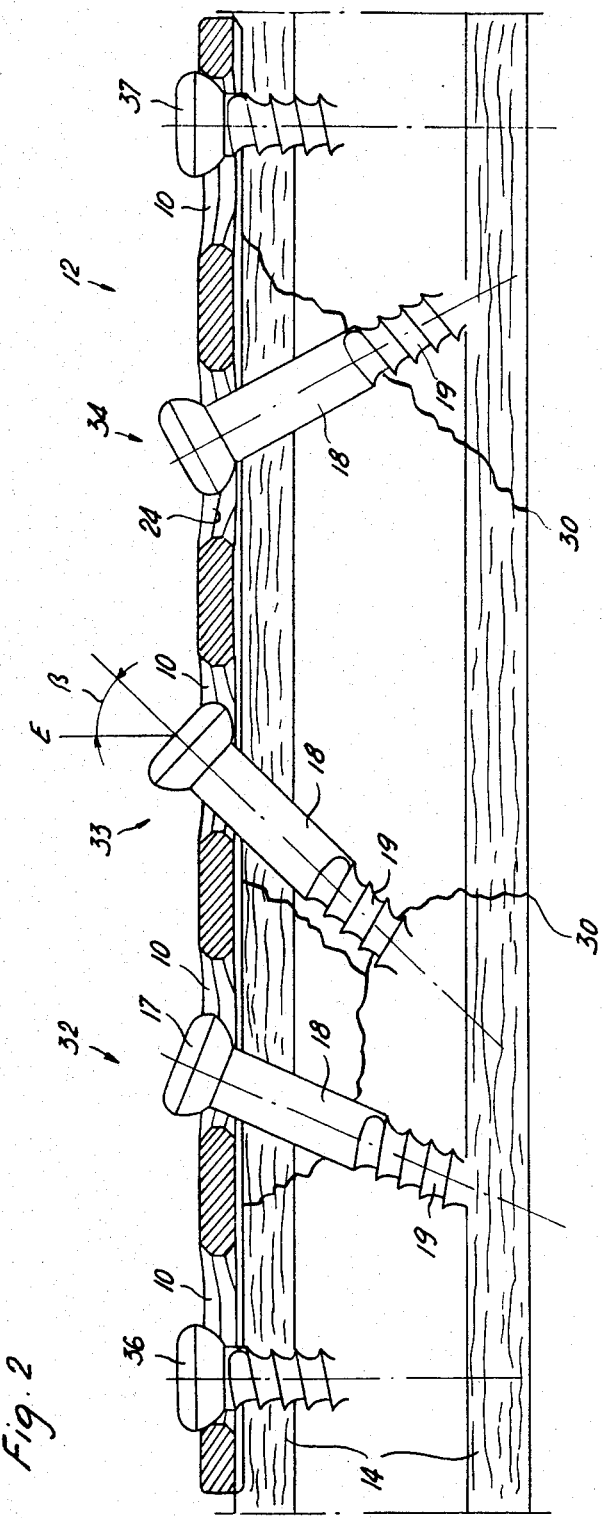
FIG. 2 is a schematic view in vertical longitudinal section showing a system according to the invention as applied to a multi-fragmented fracture.

In FIG. 2, the system according to the invention is shown applied to a multi-fragmented fracture 30 of a bone 14. The plate 12, provided with several holes 10, lies snugly but necessarily tightly on bone 14.

Three screws 32, 33, 34, each having a threadless portion 18 between screw head 17 and thread 19 are inserted transversely, in such manner that they form an angle of inclination $\beta$ with plane E perpendicular to the longitudinal axis of the hole; this angle of inclination $\beta$ may be of varying degrees for screws 32, 33, 34, and depends on the course of the fracture 30. Screws 32, 33, 34 can slide on surfaces 24 of the holes. In this instance screws whose axes are perpendicular to the longitudinal axis of the hole are also used. They serve only to fasten plate 12 to bone 14. While the number of transversely inserted screws 32, 33, 34 is dependent on the type and number of fracture points, preferably at least two plate fixation screws are used, preferably near the ends of the plate.

The screws can be provided either with a thread that requires tapping of the drill-hole or may have a self cutting thread, used with an untapped hole.

Figure 3:
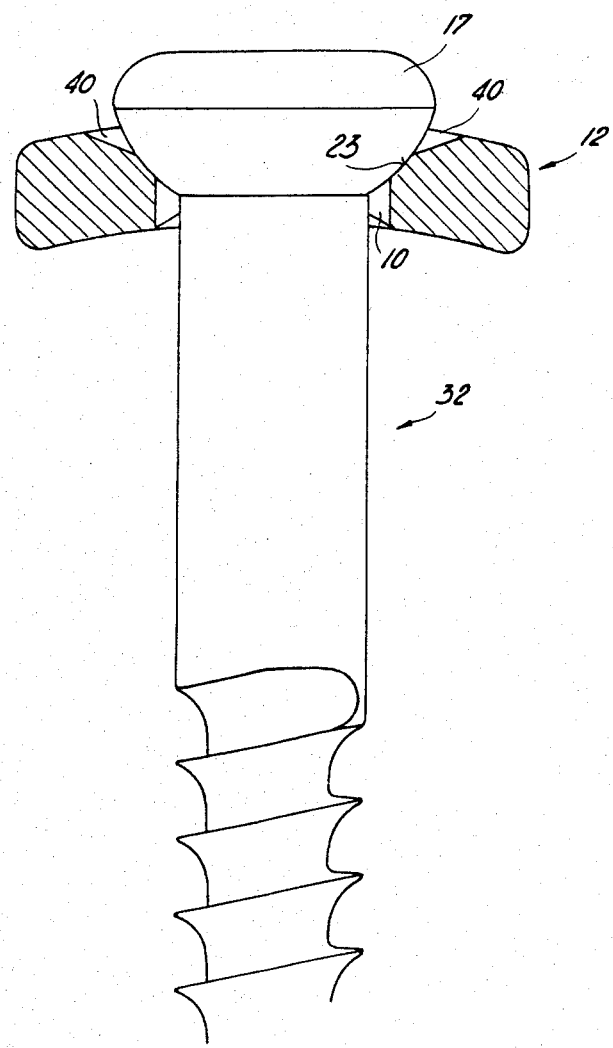
FIG. 3 is a schematic view showing in vertical transverse cross section, a plate according to the invention, with a screw, and depicting details of the hole.

FIG. 3 shows a transverse cross section of a plate 12 and a screw 32, according to the invention. As shown in FIG. 3, the edges 40 of holes 10 on the upper side of plate 12 are bevelled. This facilitates bending of the plate, if that is necessary or desired. As before the hemispherical head 17 after screw bears on the sloping surfaces 23 of the hole 10.

Figure 4:
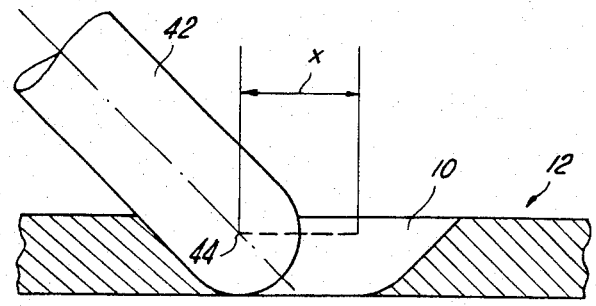
FIG. 4 is a schematic view partly in vertical section, showing a method of making a device according to the invention by milling a hole using a spherical cutter.

FIG. 4 illustrates a method of making holes in plates according to the invention. As shown, there, hole 10 is made by milling with spherical cutter 42. Mid-point 44 of the head of cutter 42 moves along stretch X during the milling process. Preferably, the cutter is computer-controlled.

Figure 5:
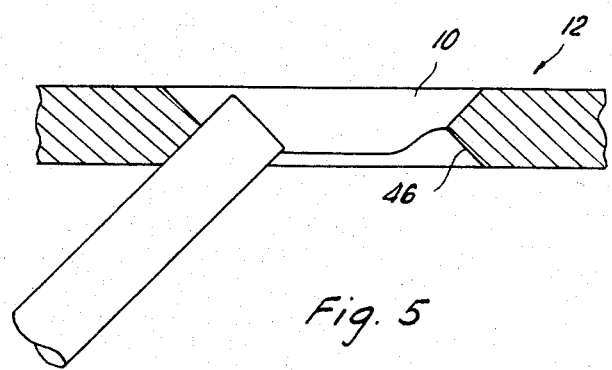
FIG. 5 is a schematic view partly in vertical section, showing a method of making a device according to the invention and particularly the milling of the funnel-shaped flare.

FIG. 5 shows formation of the funnel-shaped, flared or undercut portions 46 on the bottom of the plate by milling.

Figure 6:
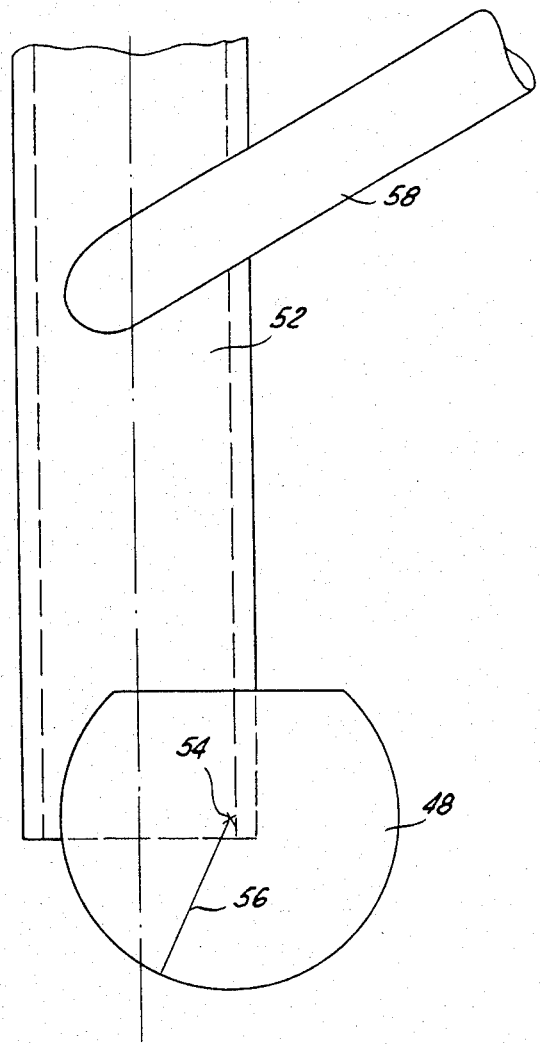
FIG. 6 is a view in side elevation of a drill guide according to the invention.
Figure 7:
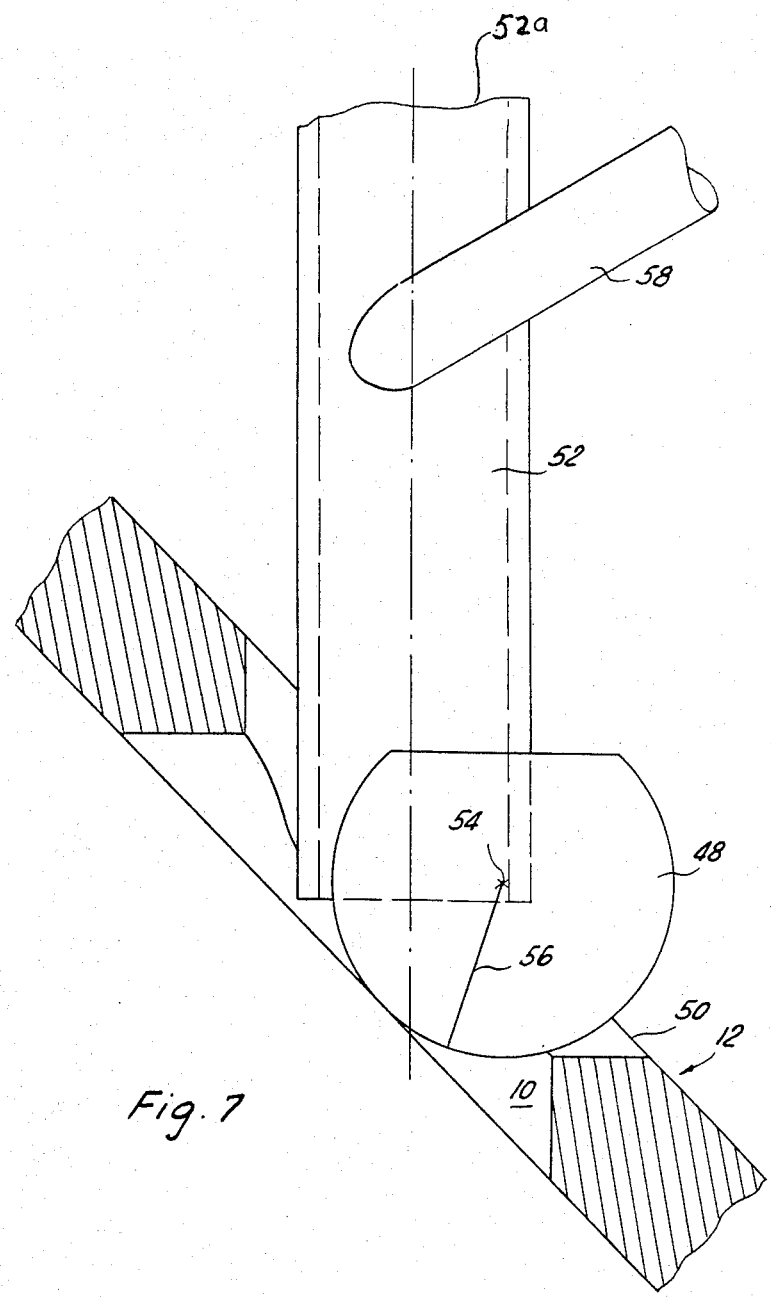
FIG. 7 is a view in elevation and partly in vertical section showing the manner of use of drill guide in accordance with the invention.

FIGS. 6 and 7 show a drill guide which may conveniently be used to drill holes in bones to be fitted with devices according to the invention. Referring to FIG. 6, a drill tube or socket 52 is connected to a ball-shaped bearing 48 having a radius 56, in such a way that the axis of the tube is eccentric to the mid-point 54 of the ball bearing 48. A shaft 58 is provided for holding the guide in position.

As shown in FIG. 7, the guide of FIG. 6 is used by fitting the bearing 48 into hole 10 of a plate 12 according to the invention. The bearing 48, being spherical, fits the cylindrical sloping surfaces of the hole. It is preferably positioned at the end of the hole and can be tilted back and forth to the desired angle by appropriate manipulation of the shaft 58. A drill (not shown) may then be inserted down the passage 52a in tube 52 to make the desired hole in the bone.

The device according to the invention has various advantages compared to conventional compression plates.

As shown in FIG. 11, the transcortical fracture column is drawn apart with known devices. Through the transverse position of the screws in the device according to the invention, double compression becomes possible, since through the lever effect, as shown in FIG. 1, both the ciscortical fracture and the transcortical fracture are pressed together. Accordingly, when using the device according to the invention, no additional measures, such as bending the plate, are normally required to close the transcortical fracture.

When using a conventional compression plate, the tension path, i.e., the distance along which the screw, including the portion of the bone held by it, is pushed in the direction of the fracture, is determined in advance. In contrast, compression with the device according to the invention can be adjusted to the prevailing circumstances during insertion of the screws, because the screws may slide in the hole and the entire hole length need not be used.

The head of the screw of the device, according to the invention, is not bent plasticly during use, that is, the upper part of the screw shaft, including the head of the screw, is not bent plasticly as a result of rotating the screw axis, e.g., by the angle 2 in FIG. 1.

In setting a fracture by means of a plate, it is desirable to have the plate as small and thin as possible, since under the plate, dissolution of the cortex, so-called spongiosis, tends to occur. This phenomenon is also designated stress-protection, since it is assumed that it occurs as a result of protection of the underlying bone area against external stress. The plate of the device according to the invention can be made very thin and small, since, as a result of the transfragmentary position of the screw, the mechanical loading on the plate is less. In conventional devices, the tolerance with reference to the eccentric screw position in the plate hole is governed by the plate thickness. Since according to the invention, the screw can slide and tilt in the direction of the plate axis, a plate practically as thin as desired can be used, because the thickness tolerance of the plate need not be exhausted.

Although the Figures show only tubular bones, the invention can also be used for the stabilization of fracture areas in other bones.

What is claimed is:

1. A surgical device for the stabilization of broken bones and for use in compression osteosynthesis comprising an elongated plate having a top surface, a bottom surface for application to a bone and a plurality of elongated holes, each of said holes having surfaces along each side sloping inwardly and downwardly, the width of said holes transversely to their longitudinal axis being constant along their length and the length greater than the width by at least one third the width, there being an undercut surface on the bottom of each of said holes at both ends thereof, said holes being symmetrical about a center line across the width of the holes.

2. The device claimed in claim 1 and including a bevelled surface running longitudinally of each of said holes connecting to the top surface of the plate and to said sloping surfaces.

3. The device claimed in claim 1 wherein the sloping surfaces are cylindrical.

4. The device claimed in claim 1 wherein the sloping surfaces are compound surfaces defined by two planes intersecting in a line parallel to the longitudinal axis of the hole.

5. The device claimed in claim 1 wherein the longitudinal axis of at least one of said holes is parallel to the longitudinal axis of the plate.

6. The device claimed in claim 1 wherein the longitudinal axis of the hole is oblique with respect to the longitudinal axis of the plate.

7. The device claimed in claim 1 wherein the longitudinal axis of at least one of said holes is at a right angle to the longitudinal axis of the plate.

8. A system for the stabilization of broken bones and for use in compression osteosynthesis comprising an elongated plate having a top surface and a bottom surface for application to a bone, a plurality of elongated holes in said plate and a plurality of screws adapted to pass through said holes to engage the bone, each of said screws having a head and a shank, the portion of said shank nearest the screw head being free from threads, the length of said holes being greater than the maximum diameter of the shank of said screws by at least one-third said diameter, there being surfaces along each side of said holes to provide for sliding movement of said screws axially of said plate, and an undercut surface at the bottom of each of said holes at at least one end thereof.

9. The system claimed in claim 8 wherein the slope of the undercut surface is such as to permit insertion of a screw at an angle of 45°.

10. The system claimed in claim 8 wherein the unthreaded portion of at least one of said screws has a diameter at least as great as the largest diameter of the threaded portion.

11. A drill guide for drilling holes in a bone said guide comprising a drill socket and a ball-shaped bearing, said socket being attached to said bearing in a position eccentric to the center of the ball.

* * * * *